United States Patent [19]

Meuzelaar et al.

[11] Patent Number: 4,980,131

[45] Date of Patent: Dec. 25, 1990

[54] MICRO-VOLUME, CURIE-POINT PYROLYSIS/DESORPTION APPARATUS

[76] Inventors: Henk L. Meuzelaar; William H. McClennen, both of U of U, EMRL Rm. 214, Salt Lake City, Utah 84112

[21] Appl. No.: 198,063

[22] Filed: May 24, 1988

[51] Int. Cl.$^5$ ............... G01N 31/22; G01N 25/22
[52] U.S. Cl. ............................ 422/78; 436/158
[58] Field of Search .................. 422/78; 436/156–160

[56] References Cited

U.S. PATENT DOCUMENTS

| | | | |
|---|---|---|---|
| 3,703,355 | 11/1972 | Takahashi et al. | 422/78 |
| 3,726,646 | 4/1973 | Kravetz et al. | 422/78 |
| 4,408,125 | 10/1983 | Meuzelaar . | |
| 4,601,882 | 7/1986 | Benner | 436/157 |
| 4,710,354 | 12/1987 | Behar et al. | 436/157 |
| 4,824,792 | 4/1989 | Thorpe et al. | 436/157 |

OTHER PUBLICATIONS

Curie Point Pyrolysis for GC— or MS–Application Pyrola–A New Horizon for Materials Analysis.
Pyrojector—For Pyrolysis Analysis with Packed and Capillary Gas Chromatography.
Curie Point Pyrolysis and Automatic Samples for GC—, IR— or MS–Application.
"Simple Pyrolysis Chamber Modification for Capillary Column Curie–Point Pyrolysis Gas Chromatography—Mass Spectrometry of Complex Biomaterials" Journal of High Resolution Chromatography and Chromatography Communications, 1986.

Primary Examiner—Robert J. Warden
Assistant Examiner—Lyle Alfandary Alexander
Attorney, Agent, or Firm—Thorpe, North & Western

[57] ABSTRACT

A pyrolysis/desorption apparatus for use with chromatographic and spectroscopic detection systems for providing chemical analysis of samples. The device includes a tubular body having an interior reaction chamber which houses a pyrolysis/desorption probe adapted for bearing a coating of the sample composition to be analyzed. A separating tube is positioned within the reaction chamber, at a slightly displaced distance from the probe for receiving reaction product entrained within a carrier gas. A carrier gas inlet is coupled to the tubular body upstream from a portion of the reaction chamber and operates to introduce carrier gas flow through the reaction chamber and toward an opposing end of the tubular body. A carrier gas outlet is located down stream from the reaction chamber for venting carrier gas and entrained reaction products which are not split off by the separating tube. This separating tube is of substantially smaller cross section than the cross section of the reaction chamber to enable increased speed of analysis and increased control of product flow. The system is adapted with means for maintaining carrier gas flow at a speed greater than the back diffusion rate of possible contaminant materials within the tube which may exist down stream of the reaction chamber.

11 Claims, 7 Drawing Sheets

CARRIER GAS

MICRO-VOLUME, CURIE-POINT PYROLYSIS/DESORPTION APPARATUS

BACKGROUND OF THE INVENTION

1. Field of the Invention

The present invention relates to a method and apparatus for chemical analysis by pyrolysis and thermal desorption techniques, and more particularly to a method and apparatus for Curie-Point Pyrolysis and/or desorption of complex, nonvolatile test samples.

2. Prior Art

Pyrolysis techniques have long been applied in analysis of macromolecules, particularly for complex molecular structures. In simple terms, the process involves the thermal fragmentation of the molecule into characteristic component parts. Analysis of these smaller molecules by standard techniques such as mass spectroscopy (MS) and/or gas chromatography (GC), develops predictable test results when performed under similar conditions. In other words, pyrolysis of a given compound at a given temperature and controlled environment will produce the same family of component molecules in a predictable manner. Such results can be readily evaluated from a mass spectrum or chromatogram.

Curie-Point pyrolysis has provided a relatively simple technique for reproducing a specified temperature for the fragmentation reaction and utilizes a wire comprised of ferromagnetic material to position a coating of the sample within a reaction zone. See, for example, U.S. Pat. No. 4,408,125 by Meuzelaar. At the Curie-point of a temperature range, the ferromagnetic material loses its magnetic properties and therefore fails to inductively absorb energy from an associated electromotive source. Peak temperature of the wire is accordingly stabilized at the Curie-point temperature, providing reproducible character to the reaction zone. Ideally, predictable fragmentation products can then be produced for identical samples, assuming a common temperature/time profile.

The degraded components of the reaction are then conducted to an inlet of the analysis device for detection. Generally, the pyrolysis apparatus is integrated with the analysis system (GC, MS, etc) in a manner such that fragment transfer is reproducible with similar repetitive efficiency and accuracy as is the pyrolysis reaction. Failure to control sample transfer can materially alter output of the detection device, as well as mask the sample results with unwanted background detection.

The prior art has suggested that apparatus design provide for total transmission of volatile products for analysis. Efficient transmission of volatile products requires (a) rapid removal from the reaction zone to avoid secondary reactions (e.g., secondary pyrolysis or recombination reactions), (b) minimization of condensation losses on the reactor walls and (c) rapid transfer into the detecting instrument (e.g., gas chromatograph and or mass spectrometer). These general principles are well recognized in modern textbooks, on analytical pyrolysis such as: *Analytical Pyrolysis,* William J. Irwin, Marcel Dekker, Inc., (1982) p49. This author suggests that in pyrolysis mass spectrometry, the pyrolyzer should be within the ion source of the mass spectrometer if at all possible. Similarly, GC procedures should involve minimization of gas diffusion by conducting pyrolysis as near to the column top as possible and with the unit located within the column heater zone to avoid condensation onto cool surfaces.

Most of the above design considerations with regard to efficient and rapid sample transfer also apply when the objective is to desorb intact, low volatile compounds rather than to effect pyrolysis. In fact, many complex samples consist of a mixture of more or less volatile components which can be thermally desorbed and nonvolatile components which need to be pyrolyzed in order to enable transfer to the detector.

A typical example of the use of a Curie-point heating device to effect thermal desorption of low volatile components is described by J. de Leeuw et al. (Analytical Chemistry, 49 (1977), 1981). The advantages of Curie-point desorption over conventional sample injection techniques using a dilute solution of the sample in a suitable solvent are: elimination of the solvent (which may adversely effect operation of the column and detector) and more rapid desorption of components (due to the high heating rates obtainable by Curie-point techniques).

Based on the aforementioned guidelines, the system design criteria adopted within the prior art have been based on coupling the reaction chamber to a receiving chamber which joins the detector inlet to the system. FIG. 1, for example, represents a basic design for implementing the above recommendations for a capillary type system. Id. p 64. This apparatus comprises a cap 1 enclosing an opening of a quartz tube 2 which receives the ferromagnetic element with coated sample, the enclosure being completed by a mounting flange 3. This area is sealed at an upper end by an O-ring 4 to a Delrin (TM) mount, which is further sealed to a pyrex tube 7 and additional Delrin mount 8 to filament enclosure for the water-cooled induction coil 6. A Teflon (TM) seal 9 abuts a lower mounting flange 10 which couples the pyrolysis component to a GC injector 11 and enclosed capillary column 12. The efficiency of this disclosed system is achieved by gas flows being routed through and around the pyrolysis tube before entering the capillary column. As with earlier designs, the object of this device is to transport all of the pyrolyzed material into the GC column. The described gas flow permits control of flow rates for the pyrolysis reaction, as well as for the flow separation within the GC column.

A particular problem arising with this conventional design is inherent with the physical and dimensional requirements of the Curie-Point reactor system. For example, the dimension of the reaction chamber must be sufficiently large to permit insertion of the sample-coated, ferromagnetic element or wire. This element must be free of contact with the inner walls of the tube forming the reaction chamber. Even though this chamber should be designed as small as possible to minimize dead space, a 2 millimeter inner diameter is necessary for use with a 0.5 millimeter inserted element. Reduction of the element dimension is difficult for reasons of heating requirements utilizing high frequencies of a typical induction source.

A principle difficulty is how to match this larger diameter, with the $\frac{1}{2}$-1/10 millimeter internal diameter for the capillary tube which is to receive the pyrolysis desorption products. In summary, the resulting problem is how to couple a relatively wide reaction chamber tube efficiently to a very narrow capillary tube.

One of the problems arising because of this mismatch is illustrated in FIG. 2. Items 20 and 21 represent capillary columns which correspond to item 12 in FIG. 1. If the pyrolyzed sample comprises components A and B occupying the volume A+B in FIG. 2a and is transferred in full into the capillary tube, chromatographic separation over the distance "x" might be illustrated by the three components A', A'+B', and B' wherein A' and B' partially overlap at A'+B'. If, however, the size of the plug within the tube is reduced in volume, operation of separation over the same distance "x" results in resolution of the components A' and B' into detectable peaks as illustrated in FIG. 2b. An option to increasing the separation is to increase the length of the tube to allow time for the components A and B to fully separate, say at a distance of 2x. Unfortunately, in many applications, time may be of the essence. A reduction in several minutes may be critical. Moreover, increased length of the column requires a higher pressure differential across the column in order to maintain adequate column flow. This in turn results in less ideal separation conditions as well as increased pressures in the reaction zone.

In addition to the problem of maintaining a small volume of sample in order to keep separation time low, current systems encounter a variety of problems which relate to contamination of pyrolyzed/desorbed samples. Such contamination can occur by change of composition within the chamber and flow line, loss of sample by condensation of pyrolysis/desorption components on tube walls and related factors that alter the detection output by increasing background signal.

An example of contamination within the flow line is the volatization of condensate remaining from prior reactions on the tube walls of the reaction chamber and flow line. Although the reaction zone may easily reach temperatures in excess of 500 degrees C., the surrounding tube walls will generally have to remain at less than 300 degrees C. in order to prevent secondary pyrolysis of reaction products. It is not uncommon, therefore, for components of the pyrolyzed/desorbed samples to condense on the cooler wall surface subsequent to pyrolysis. Any condensate not removed after previous analysis may again volatize and mingle with the new sample pyrolysis/desorption components. Obviously, the occurrence of such prior matter will give a false reading and seriously undermine the analytical value of the system. Primary attempts to solve this problem have focused on minimizing condensation and providing better control of downline reaction environment and hardware.

Unfortunately, each addition of complex hardware not only increases cost of the equipment, but adds to the complexity of operation and possibility of component failure. What is needed is a simple technique for reducing these adverse consequences within a pyrolysis/desorption system without slowing down the speed of analysis or increasing cost and complexity.

OBJECTS AND SUMMARY OF THE INVENTION

It is an object of the present invention to provide a device and method for pyrolysis/desorption which has substantially increased analysis speed and greatly reduced background noise and interference from condensate from prior reactions and other contaminants.

It is an object of this invention to provide an improved pyrolysis/desorption device and method which reduces the need for careful control of downline carrier flow and condensation.

It is a further object of the present invention to provide structural improvements to current pyrolysis/desorption apparatus which enhance the accuracy and speed of analysis procedures, particularly with gas chromatographic systems.

These and other objects are realized in an apparatus for performing pyrolysis/desorption which includes a tubular body having a longitudinal axis, first and second ends providing access to an interior volume of the tubular body, and an interior reaction chamber between the first and second ends. A pyrolysis/desorption probe is positioned within the reaction chamber and is adapted at its distal end with means for receiving a coating of sample composition to be subjected to analysis. A carrier gas inlet is coupled to the tubular body upstream from a portion of the reaction chamber near the inlet and is operable to introduce carrier gas flow through the reaction chamber and toward the second end of the tubular body. A major portion of such carrier gas is vented through the second end of the tubular body, along with any entrained reaction products. Reaction activating means are provided in association with the reaction chamber for initiating pyrolysis/desorption of the sample at the distal end of the probe. A narrow separating tube having a proximal end and an opening of substantially smaller cross sectional area than the area of the reaction chamber cross section is provided and includes positioning means for placing the proximal end and opening within the reaction chamber and slightly displaced from the distal end of the probe toward the outlet. Connecting tubing is provided for attaching the remaining end of the separating tube to a detection device such as a gas chromatograph.

The invention is practiced by coating the pyrolysis/desorption probe at its distal end with a sample composition to be subjected to analysis. This probe is positioned at its distal end within the reaction chamber. The separating tube is likewise positioned within the reaction chamber with its proximal end and opening slightly displaced from the probe and oriented toward the flow of carrier gas. The remaining end of the separating tube is attached to the detection device and a uniform flow of carrier gas is initiated through the reaction chamber, being divided between the separating tube and a venting outlet which carries most of the carrier gas and any entrained reaction product free from the apparatus and system. Pyrolysis/desorption is activated by an appropriate power source and the pyrolysis/desorption reaction then ensues. Analysis is accomplished by separating a small portion of reaction product entrained with the carrier gas into the separating tube for detection by a gas chromatograph, or other comparable detection device. Contamination of the separated gas and product is prevented by maintaining carrier gas flow speed at a value greater than diffusion rates of any reaction products developed by the pyrolysis/desorption process.

Other objects and features will be apparent to those skilled in the art based upon the following detailed description, and in view of the accompanying drawings.

DETAILED DESCRIPTION OF THE INVENTION

It has been discovered by the inventors that analytical procedures utilizing pyrolysis/desorption can be both simplified and accelerated by changing the prior art spacial positioning of the capillary tube 12 and the coated ferromagnetic element or probe positioned within the reaction chamber. Whereas prior art techniques have involved mechanically coupling the MS or GC device to the pyrolysis/desorption apparatus with a mismatch in size between the reaction chamber and capillary inlet tube, the present invention positions this capillary tube and its inlet within the reaction chamber and up stream from the mechanical coupling between the pyrolysis/desorption device and detector device.

Figure 3:
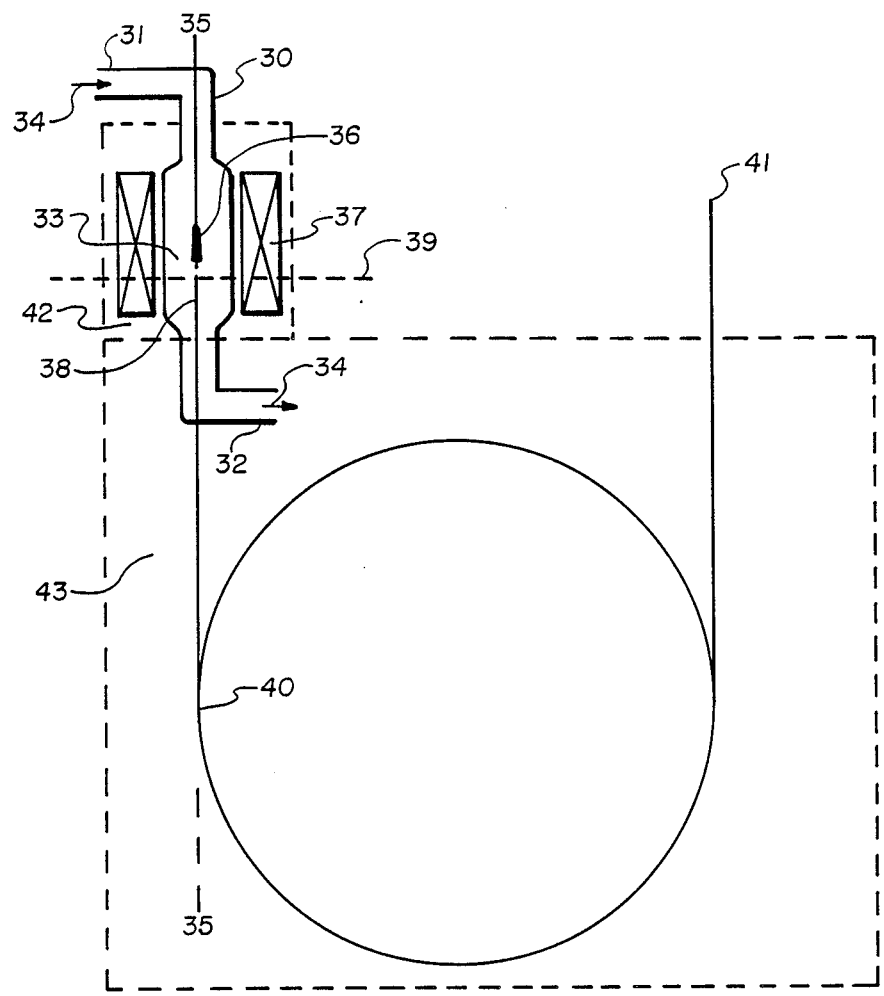
FIG. 3 is a schematic representation of central components of the pyrolysis/desorption apparatus.

This is schematically illustrated in FIG. 3 which shows a tubular body 30 having a forced end 31 and a second end 32 and an intermediate reaction chamber 33. First and second ends 31 and 32 provide access to the reaction chamber, and in particular permit flow of carrier gas 34 to and from the reaction chamber. Generally, this tubular body is symmetrically configured about a longitudinal axis 35 which is also the positioning location for the pyrolysis/desorption probe 36. The schematic embodiment shown in FIG. 3 represents a Curie-Point configuration including an induction device 37 to power the reaction.

A capillary separating tube 38 is positioned within the reaction chamber 33 and is slightly displaced from the probe 36. The purpose of such close proximity between the open receiving end of the capillary tube 38 and the reaction zone around probe 36 is described in greater detail hereafter.

For purposes of description, this relative spacial displacement between the probe and capillary opening is identified with respect to cross sectional areas. Item 39 represents an intersecting plane in orthogonal relationship with respect to the longitudinal axis 35. That portion of the plane enclosed within the reaction chamber 33 of the tubular body 30 represents the cross sectional area based on the inner diameter of the tube. Reference to the reaction chamber will generally be directed to that portion of the tubular cavity around the probe 36 and extending downward along a distance of approximately 10 millimeters from the distal end of the probe 36. The preferred reaction chamber will be that area immediately around the probe which is subject to the intense heat of reaction, and avoids the lower temperatures associated with the tubular wall, which are typically maintained at 200–300 degrees centigrade by ceramic heater element (not shown). Accordingly, the intersecting plane 39 could be defined for any section of this reaction chamber.

In a similar manner, this intersecting plane 39 is used as a reference to identify the cross sectional area of the capillary tube 38 for comparing its opening size with respect to the surrounding tubular opening of the reaction chamber 33. A primary guideline of the present invention is the opening of the capillary tube 38 be substantially smaller than the surrounding reaction chamber 33. This enables splitting off a small component of the carrier gas and entrained reaction products as shall be described in connection with FIG. 4 hereafter.

Returning to the schematic representation of FIG. 3, the capillary tube 38 continues to a sufficient length to constitute a separation column 40 which feeds its separated components, which are discharged 41 into a detection device. The small area 42 enclosed within phantom lines represents the heated zone at approximately 200 degrees centigrade. The larger enclosure 43 represents the gas chromatographic oven of conventional form.

This gas chromatographic system is just one of many examples involving the use of analytical pyrolysis/desorption. Its applications include analysis of complex nonvolatile samples, including synthetic polymers, geopolymers and biopolymers as well as of low volatile samples, including drugs, metabolites, natural substances and oligomers. The analytical pyrolysis/desorption methods utilizing GC or MS detectors have impressive specificity for the analysis of polymer structure and investigation of thermal stability properties. The above schematic description represents a departure from prior techniques of sample injection to a philosophy which brings the capillary tube 38 directly within the reaction chamber 33 and proximate to the probe 36. By utilizing this close spacial relationship, along with controlled speed of the carrier gas with respect to diffusion rates of reaction products, prior concerns for low dead space and contamination by condensate have been substantially reduced. In fact, with the present apparatus, one need have little concern for condensate or other contamination below the opening of the capillary tube 38, thereby avoiding replacement of the tube after each analysis.

The subject device has been tested in experiments utilizing a Tracor 560 gas chromatograph equipped with a 15 meter×0.32 i.d. column coated with 0.25 um of DB-5 (J and W Scientific). A Fisher 0310 Curie-Point power supply operating at 1.5 kW and 1 MHz was used for heating the sample probe. A mass spectrometer was utilized to detect reaction product and consisted of the Finnigan MAT 700 Ion Trap Detector with version 3.01 software operating on an IBM PC-XT.

The components of the pyrolysis/desorption apparatus included a 1.5 millimeter id pyrex glass reaction tube, representing tubular body 30. Samples of various compositions were dissolved and/or finely suspended in methynol and were placed on the ferromagnetic filament or probe 36, and were allowed to dry. The filament was then drawn into the pyrolysis tube 30 and helium carrier gas 34 and gas flow was initiated at 2.8 milliliters per minute. This reaction tube was then inserted into a pre-heated injector, sealing and conventional O-ring assembly and adjusting the capillary tube 38 to within approximately 2 millimeters of the probe 36. The injector backflush was shut off and the reactor was fired for 0.6 to 2.0 seconds within 10 to 40 seconds after initial insertion. The results of actual experiments are set forth hereafter with "pyrograms" representing three different compositions in FIGS. 6, 7 and 8.

Figure 4:
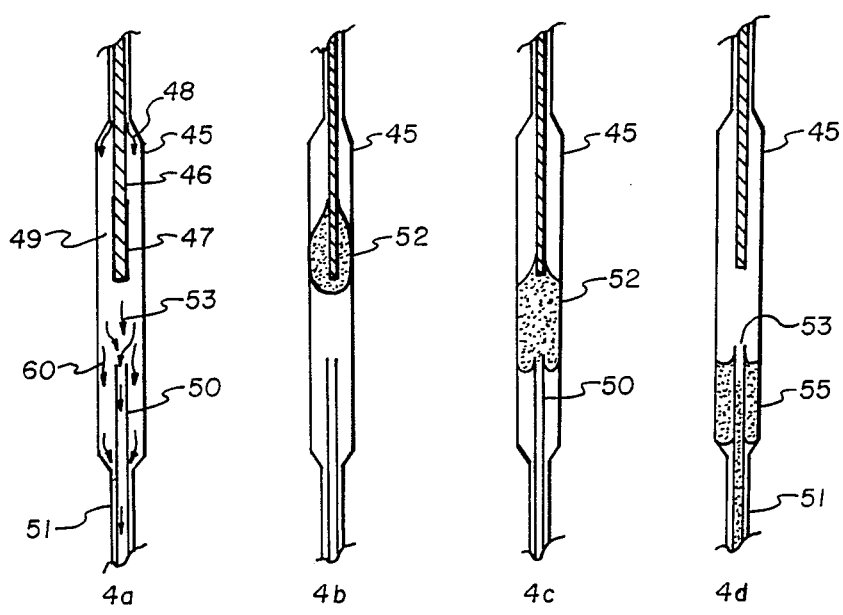
FIG. 4 includes FIGS. 4A, 4B, 4C and 4D graphically illustrating sequential stages of pyrolysis/desorption and separation of pyrolysis/desorption reaction products.

FIG. 4 illustrates an idealized mass transfer sequence for pyrolysis of polystyrene. The tubular structure 45 represents item 30 in the schematic view of FIG. 3. The filament 46 is coated with polystyrene 47, carrier gas 48 flows around the filament and into the reaction chamber 49. Initially, the walls of the reaction chamber are preheated to 200 degrees centigrade in the reaction chamber immediately below the distal end of filament 46. Carrier gas flow rate through the chamber is identified at 12.5 centimeters per second at the start of induction heating. A portion of this carrier gas flow was split off into the capillary tube 50 and has a flow speed of 50 centimeters per second. The remaining carrier gas is vented through a second end 51 of the device of the tubular body 45.

After 80 milliseconds of heating, the polystyrene is fragmented to styrene monomer 52, which monomer begins to migrate with carrier gas along the flow line 53. See, for example, FIG. 4B. 120 milliseconds later (FIG. 4C) the styrene monomer 52 reaches the capillary column 50, which splits off a portion of the monomer. 160 milliseconds later, the plug of monomer passes the capillary opening 53, with the majority of carrier gas and product 55 being vented through the second end 51. By splitting off this small component of reaction product and carrier gas, chromatographic separation and resolution of each component into separate plugs as shown in FIG. 2B can be rapidly accomplished.

It will therefore be apparent to those skilled in the art that the selection of cross section area for the capillary tube as compared to the cross section area of the main flow line at the point of splitting (at the opening 53) may be selected to control the amount of sample injected. As shown in FIG. 2B, the smaller the amount of sample, the more rapid the separation can be accomplished. The designer of apparatus may select, for example, flow rates within the reaction chamber and second opening at 10 to 100 times the flow rate through the actual capillary column 53.

A second advantage of using the splitter arrangement shown in the present invention, is the ability to control back flow of contaminants, thereby reducing background signal. This is accomplished by insuring that the flow speed of carrier gas at point 60 is greater than the diffusion rate of any contaminant which may exist on the tube walls or other structure below the opening of the capillary 53. Maintenance of this relative flow requirement insures that any prior products which may have condensed within the lower tube section of the tubular body 45 cannot diffuse and enter as an apparent reaction product in a current analysis. Accordingly, the splitting technique and relative flow rate requirements cooperate in a synergistic manner to both speed up test procedures and increase sensitivity and accuracy of detection for particular molecular structures.

Figure 5:
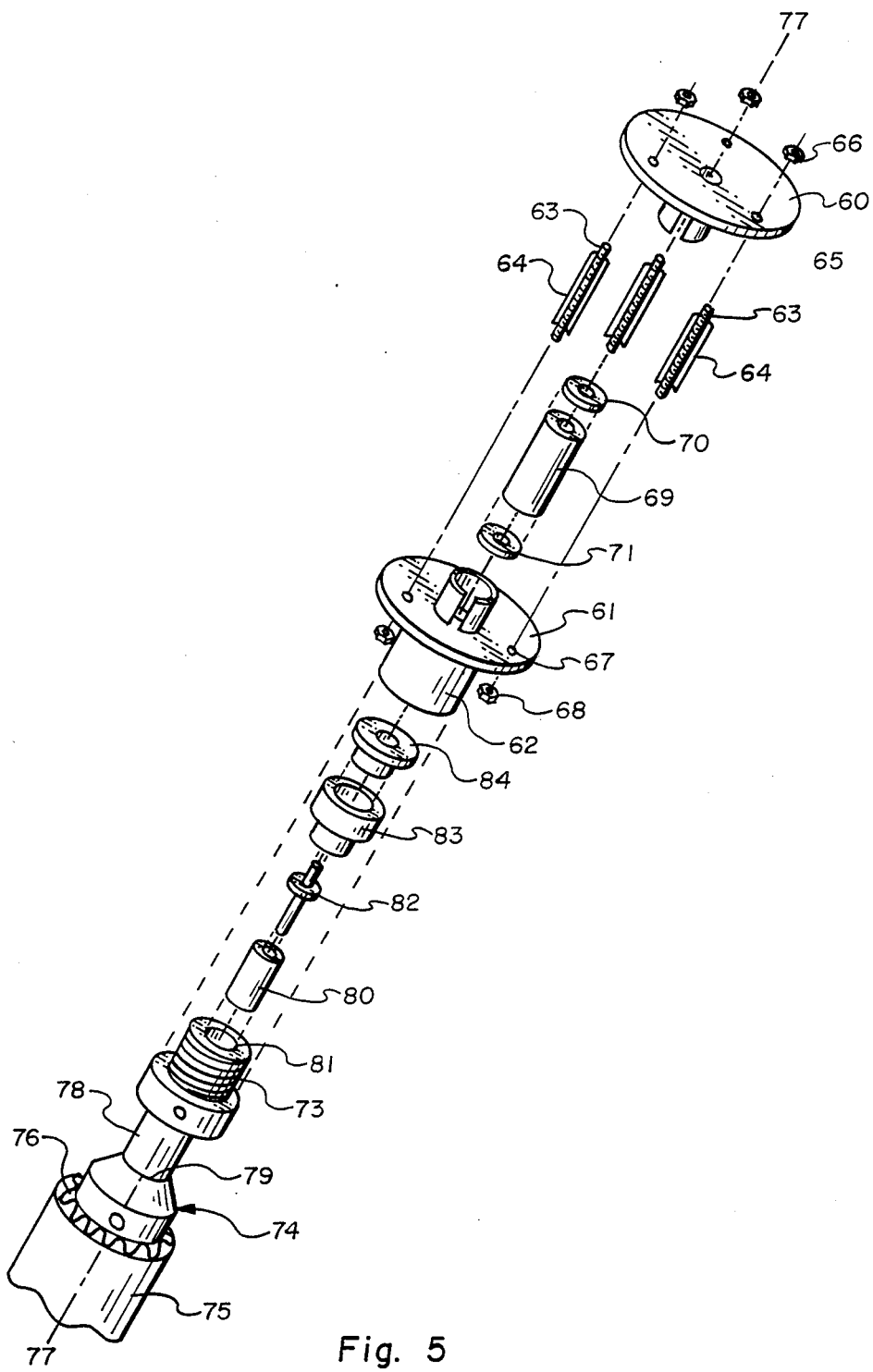
FIG. 5 is an exploded view of a pyrolysis device constructed in accordance with the present inventive principles.

A more detailed representation of apparatus structure is shown in FIG. 5. These respective components are assembled to form the casement and positioning hardware into which the reaction chamber such as is shown in FIG. 4 may be inserted. This apparatus includes a cover plate 60 which, like most of the other components is constructed of stainless steel because of the high temperature environment experienced. This plate is coupled to a retaining plate 61 and cylindrical housing 62 by means of screws 63 which are enclosed by sleeve spacers 64 (shown in half section). The upper end of each screw is coupled through an opening 65 within the cover plate and is secured by a knot 66. Corresponding attachment is provided through an opening 67 in the retaining plate, the screw being secured by knot 68. A ceramic heater element 69 is secured between these plates 60 and 61 and is electrically isolated by ceramic washers 70 and 71. This heater element 69 provides the means for maintaining the pyrolysis tube at the conventional 200–300 degree C. pre-heated temperature. An HF induction coil would be positioned around this ceramic element for Curie-Point applications. The retaining cylinder 62 mates with the threaded male end 73 of a chuck assembly 74. This chuck includes a conventional control sleeve 75 with geared teeth 76 to provide axial adjustment of the ferromagnetic filament and probe (not shown) along axis 77. A cylindrical shaft 78 is spot welded to the chuck 79 and houses an axial displacement member for controlling movement of the ferromagnetic element. A housing spacer 80 is adapted to slide within receiving chamber 81. This spacer operates to provide a thorough seal at an O-ring (not shown) which is associated with fitting 82 which telescopically is received within the spacer housing 80 and ferro 83. Ferro cap 84 operates to effectively seal an upper end of this assembly of elements 80, 82 and 83, which are collectively housed within the cylindrical chamber of element 62. This seal is established by proper placement of the retaining plate and cylinder 61, 62 in its mated position on threaded member 73. A reaction chamber such as is illustrated in FIG. 4 is positioned within this assembly 80–84, and a capillary tube (50 in FIG. 4) is introduced along axis 77 through the cover plate 60 and into the reaction chamber housed within the assembly 80–84. Carrier gas is introduced in conventional manner and provides an operable system which is fully sealed against external contamination and which implements the splitting technology disclosed herein to control flow rates and to prevent contamination from condensate and other internal contaminants.

Figure 6:
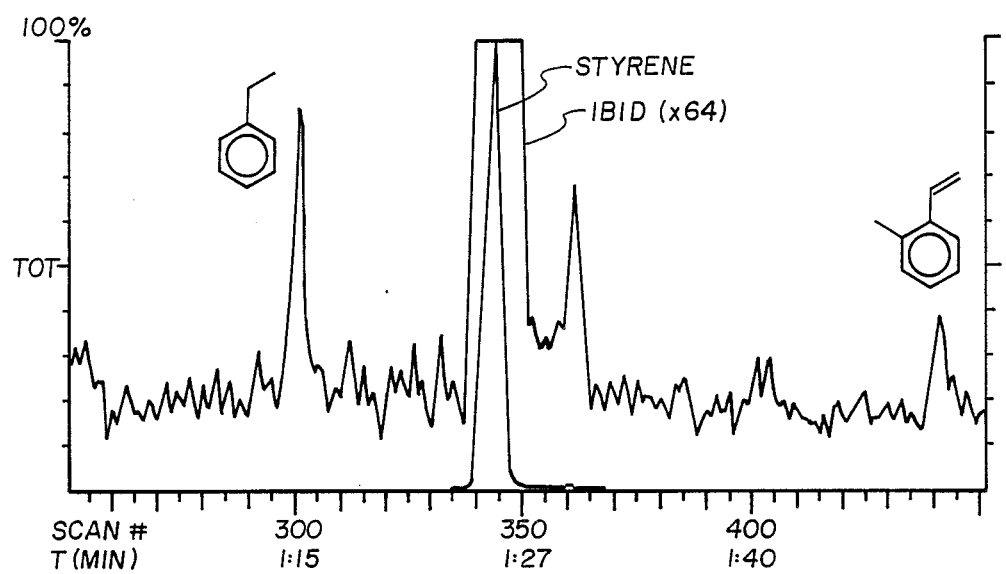
FIG. 6 is a chromatogram showing an analysis of a polystyrene sample.
Figure 7:
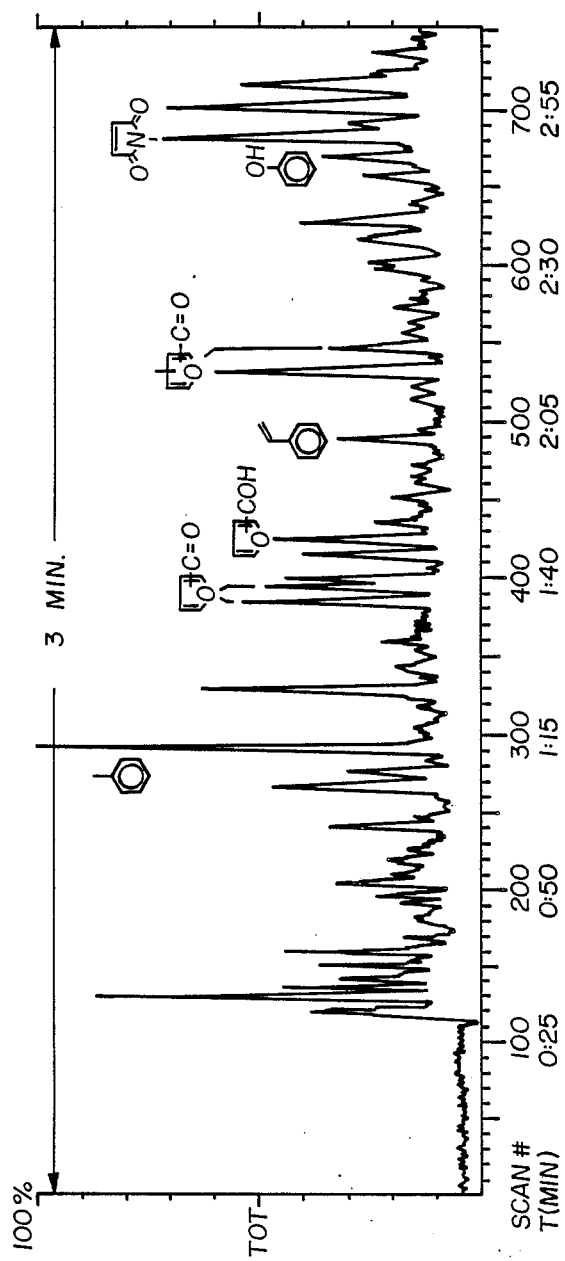
FIG. 7 illustrates a chromatogram of a streptococcus bacteria subjected to the pyrolysis/desorption procedure.
Figure 8:
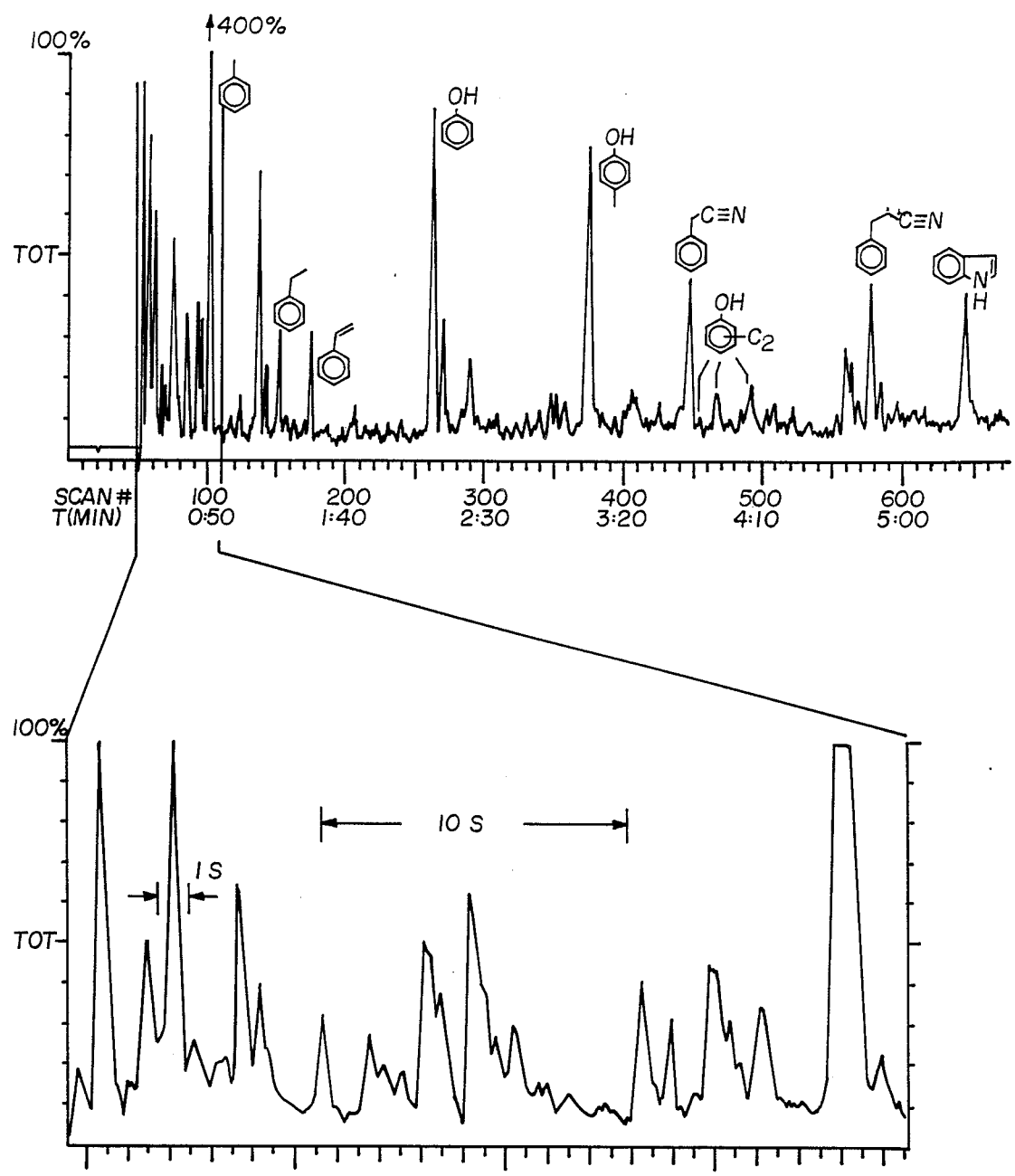
FIG. 8 illustrates a chromatogram of a protein including an enlarged portion representing the first 50 seconds of the procedure.

The examples in pyrograms represented in FIGS. 6, 7 and 8 illustrate the wide product boiling range, high sensitivity, short analysis time and high resolution capabilities of this reaction chamber configuration. In addition to the previous perameters set forth for the described experiments, the open split vent on the masked spectrometer transfer line was simply closed briefly to pressurize the tail of the column and minimize exposure of the column stationary phase to air during the sample change. The GC was programmed from 30 to 40 to 250 or 280 degrees centigrade at 15 or 20 degrees centigrade/minute and data acquired in full scans from m/z 50 to 240 at 2 or 4 scans/second or, in one case, m/z 50 to 112 at >6 scans per second.

Figure 1:
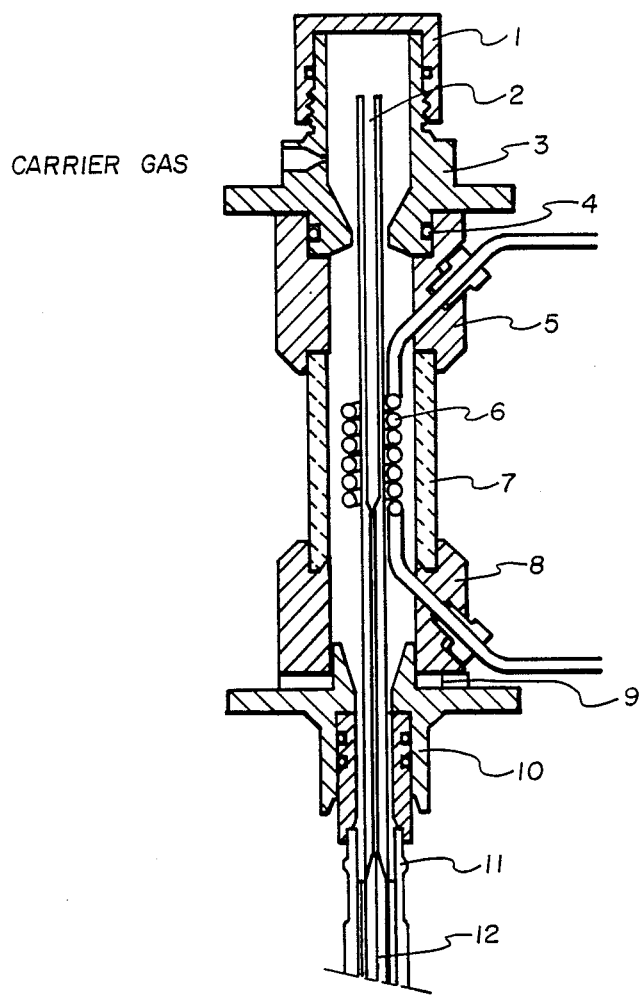
FIG. 1 shows a prior art embodiment of a Curie-Point Pyrolysis/Desorption device.
Figure 2:
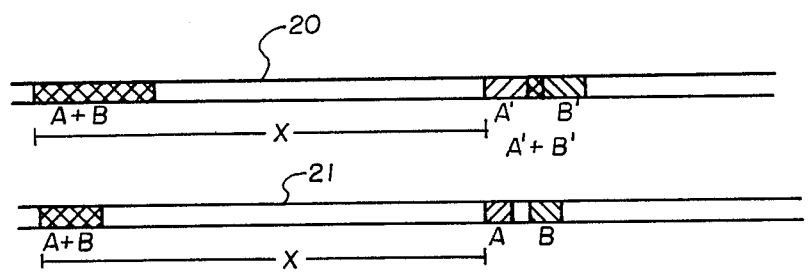
FIG. 2 shows a graphic representation of chromatographic separation of separate components A and B.

FIG. 2 illustrates a partial pyrogram of polystyrene. 78 nanograms of sample were coated on the probe and subjected to pyrolysis. The pyrogram illustrates remarkably high sensitivity (S/N ratio of styrene monomer peak approximately 250:1).

The pyrogram set forth in FIG. 3 represents a Streptococcus bacteria and illustrates the feasibility of utilizing the present invention for obtaining detailed GC information in a short duration of less than three minutes.

FIG. 8A demonstrates the application of the present invention for determination of albumin protein. The expanded high scan rate chromatograms of this albumin sample shown in FIG. 8B clearly show the high GC resolution aforded by the present reaction chamber configuration, giving peaks often less than 1 second wide.

Figure 9:
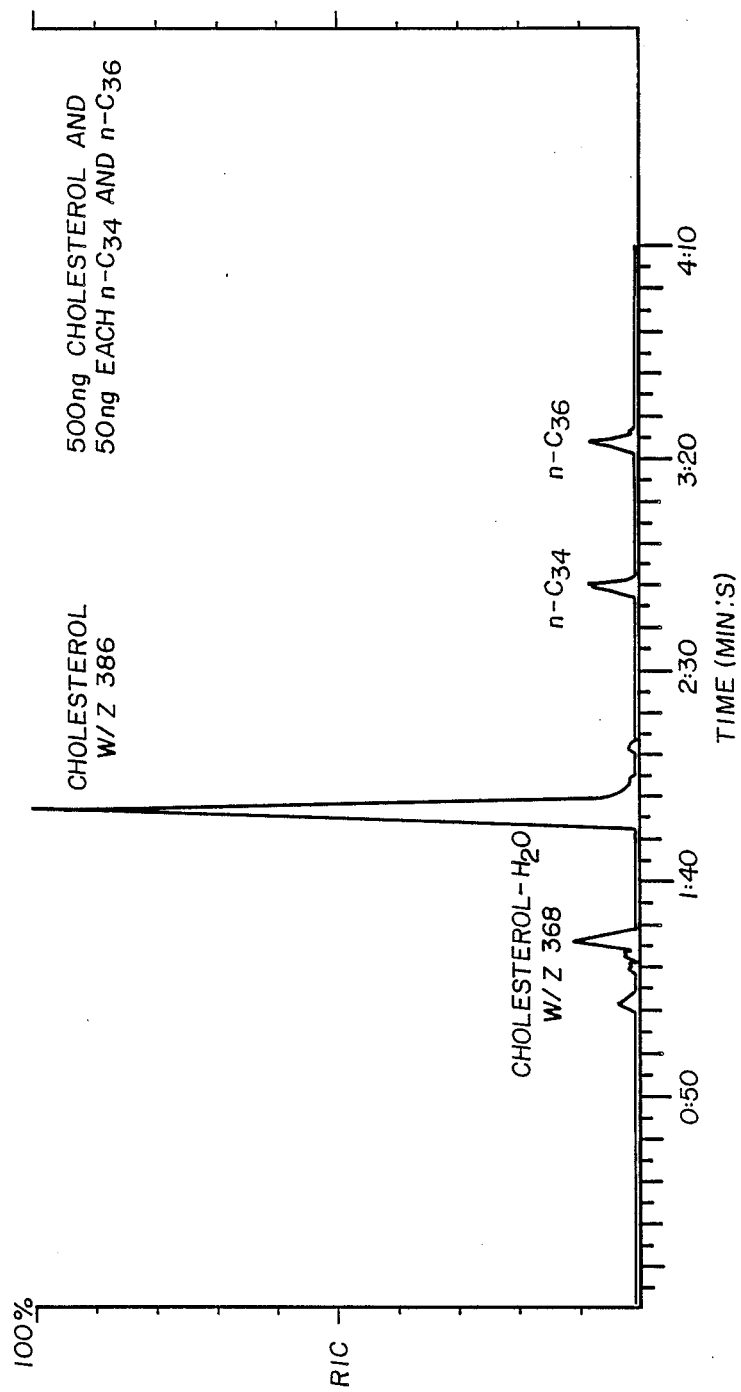
FIG. 9 illustrates application of the present invention as part of a desorption process.

Finally, FIG. 9 demonstrates the use of the present invention for effecting thermal desorption of low volatile compounds. A relatively labile substance such as cholesterol (MW 386) can be desorbed with minimum thermal decomposition (note the small water loss peak with MW 368). Two straight chain hydrocarbon compounds with 34 and 36 carbon atoms, respectively, are readily desorbed as well.

It is to be understood that the embodiments described in this disclosure are merely exemplary and are not to be considered to be limiting. It is intended that variations within the inventive concepts be comprehended within the following claims, which define the legal invention.

We claim:

1. An apparatus for performing pyrolysis/desorption with respect to samples of materials or compositions as part of a chemical analysis, said apparatus comprising:
    a tubular body having a longitudinal axis, first and second ends for providing access to an interior volume of the tubular body and an interior reaction chamber within the interior volume between the first and second ends;
    a pyrolysis/desorption probe to be positioned within the reaction chamber and adapted at a distal end with means for receiving a coating of sample composition to be subjected to analysis;
    positioning means associated with the tubular body for positioning the distal end of the probe within the reaction chamber;
    said reaction chamber being of known cross-sectional area as measured with respect to an orthogonal lane intersecting the axis between the distal end of the probe and the second end of the tubular body;
    a carrier gas inlet coupled to the tubular body near the first end and upstream from a portion of the reaction chamber, said inlet being operable to introduce carrier gas flow for delivery through the reaction chamber toward the second end of the tubular body;
    a carrier gas outlet located near the second end and downstream from the reaction chamber and being associated with the second end of the tubular body for venting carrier gas and entrained reaction products;
    reaction activating means associated with the reaction chamber for activating pyrolysis/desorption of sample disposed at the distal end of the probe;
    a separating tube enclosed within the tubular body and extending into the carrier gas outlet having a proximal end and an opening of sufficiently smaller cross-section than the area of the reaction chamber cross-section to allow gas flow within the tubular body to pass both inside and outside the separating tube, said opening being adapted for splitting off a small portion of reaction product with carrier gas from the pyrolysis/desorption reaction and dividing such separated product from the product and gas flowing within the tubular body but outside the separating tube to be vented, said proximal end being positioned near the reaction chamber and slightly displaced downstream from the probe toward the second end with the opening being oriented toward the flow of carrier gas; and
    connecting means for attaching a remaining end of the separating tube to a detection device adapted to detect product of the pyrolysis/desorption.

2. An apparatus as defined in claim 1, wherein the flow speed of the carrier gas within the reaction chamber is greater than the back diffusion rate of the reaction products or potential contaminants within the reaction chamber.

3. An apparatus as defined in claim 1, wherein the proximal end of the separating tube is positioned within a range of one to ten millimeters distance of the distal end of the probe.

4. An apparatus as defined in claim 3, wherein the proximal end of the separating tube is positioned within a range of two to six millimeters distance of the distal end of the probe.

5. An apparatus as defined in claim 1, wherein the separating tube comprises a capillary tube positioned within an enclosing tube having an inner diameter substantially larger than the outer diameter of the separating tube.

6. An apparatus as defined in claim 5, wherein the inner diameter of the enclosing tube is at least two times greater than the outer diameter of the separating tube.

7. An apparatus as defined in claim 5, wherein the inner diameter of the enclosing tube is at least four times greater than the outer diameter of the separating tube.

8. A reaction chamber for use as part of a pyrolysis/desorption device for analysis of chemical compositions based on identification of reaction products entrained within a carrier gas flow line, said chamber comprising:
    an inlet for carrier gas;
    a pyrolysis/desorption probe positioned within the reaction chamber and adapted at a distal end with means for receiving a coating of sample composition to be subjected to analysis;
    a carrier gas outlet located downstream and at an opposing end of the reaction chamber from the inlet for venting carrier gas and entrained reaction products;
    a separating tube positioned within the reaction chamber and extending into the carrier gas outlet and having a proximal end and an opening with an outer diameter of sufficiently smaller cross-section than an inner diameter of an axially corresponding cross-section of the reaction chamber to permit gas flow around and outside the separating tube, said opening being adapted for receiving a small portion of reaction product with carrier gas from the pyrolysis/desorption reaction and dividing such separated product from the product and gas flowing around the separating tube to be vented; and
    means for coupling the separating tube to a detection device capable of detecting reaction product.

9. A device as defined in claim 8, further comprising means for maintaining carrier gas flow speed at a value in excess of back diffusion rates of all reaction products.

10. A device as defined in claim 8, wherein the ratio of inner diameter cross-sectional areas of separating tube to inner diameter of the reaction chamber is at least as great as 1:2.

11. A device as defined in claim 8, wherein the opening of the separation tube is positioned toward the outlet and within one to ten millimeters of the distal end of the probe.

* * * * *